(12) United States Patent
Ledford

(10) Patent No.: US 8,209,060 B2
(45) Date of Patent: Jun. 26, 2012

(54) UPDATING SYRINGE PROFILES FOR A SYRINGE PUMP

(75) Inventor: Ricky L. Ledford, Little Canada, MN (US)

(73) Assignee: Smiths Medical ASD, Inc., Rockland, MA (US)

(*) Notice: Subject to any disclaimer, the term of this patent is extended or adjusted under 35 U.S.C. 154(b) by 281 days.

(21) Appl. No.: 12/612,720

(22) Filed: Nov. 5, 2009

(65) Prior Publication Data
US 2011/0106318 A1    May 5, 2011

(51) Int. Cl.
*G06F 19/00* (2006.01)

(52) U.S. Cl. ... 700/282; 700/87; 707/758; 707/E17.044; 604/151

(58) Field of Classification Search ............ 700/87, 700/282; 707/758, E17.044; 604/151
See application file for complete search history.

(56) References Cited

U.S. PATENT DOCUMENTS

| | | | |
|---|---|---|---|
| 5,781,442 A | 7/1998 | Engleson et al. | |
| 6,519,569 B1 | 2/2003 | White et al. | |
| 6,671,563 B1 | 12/2003 | Engelson et al. | |
| 6,731,989 B2 | 5/2004 | Engleson et al. | |
| 6,790,198 B1 | 9/2004 | White et al. | |
| 6,799,149 B2 * | 9/2004 | Hartlaub | 702/188 |
| 6,915,170 B2 | 7/2005 | Engleson et al. | |
| 6,945,954 B2 | 9/2005 | Hochman et al. | |
| 7,096,072 B2 | 8/2006 | Engleson et al. | |
| 7,103,419 B2 | 9/2006 | Engleson et al. | |
| 7,107,106 B2 | 9/2006 | Engleson et al. | |
| 7,117,041 B2 | 10/2006 | Engleson et al. | |
| 7,150,724 B2 * | 12/2006 | Morris et al. | 604/131 |
| 7,171,277 B2 | 1/2007 | Engleson et al. | |
| 7,236,936 B2 | 6/2007 | White et al. | |
| 7,403,769 B2 * | 7/2008 | Kopra et al. | 455/414.1 |
| 7,471,994 B2 * | 12/2008 | Ford et al. | 700/282 |
| 7,475,078 B2 * | 1/2009 | Kiilerich et al. | 1/1 |
| 7,483,756 B2 | 1/2009 | Engleson et al. | |
| 7,627,888 B2 * | 12/2009 | Ganesan et al. | 725/92 |
| 7,645,258 B2 | 1/2010 | White et al. | |
| 7,930,066 B2 * | 4/2011 | Eliuk et al. | 700/245 |
| 2003/0229311 A1 * | 12/2003 | G. Morris et al. | 604/151 |
| 2006/0259195 A1 * | 11/2006 | Eliuk et al. | 700/245 |
| 2007/0156779 A1 * | 7/2007 | Ho et al. | 707/201 |
| 2007/0213598 A1 * | 9/2007 | Howard et al. | 600/300 |
| 2008/0194175 A1 * | 8/2008 | Last et al. | 446/302 |
| 2008/0306437 A1 | 12/2008 | Jacobson et al. | |
| 2009/0203329 A1 * | 8/2009 | White et al. | 455/90.1 |
| 2009/0227855 A1 * | 9/2009 | Hill et al. | 600/365 |
| 2009/0234275 A1 | 9/2009 | Jacobson et al. | |
| 2009/0234285 A1 | 9/2009 | Jacobson et al. | |
| 2009/0234286 A1 | 9/2009 | Jacobson et al. | |
| 2009/0254037 A1 * | 10/2009 | Bryant et al. | 604/151 |
| 2009/0327288 A1 * | 12/2009 | Silverman et al. | 707/6 |

OTHER PUBLICATIONS

"BAS: Queen Bee", MF-9040 Instruction Manual, Bioanalytical Systems, Inc, Jan. 1996.*

(Continued)

*Primary Examiner* — Michael D Masinick
(74) *Attorney, Agent, or Firm* — Wood, Herron & Evans, LLP

(57) ABSTRACT

A method and system to update a syringe pump is provided. The pump supports a syringe having a plunger and includes a piston drive to couple to the plunger, a processor to control movement of the piston drive, and a memory to store syringe profiles for different syringes. Each syringe profile contains data for the processor to control the piston drive to expel fluid from a respective syringe at a rate. The method includes, with a computing system containing a database of data correlated to an array of syringes for which the pump could be used, culling from the database a syringe profiles for the syringes to be used by the pump within the facility or portion thereof, and updating the memory of the pump while in the facility with the culled syringe profiles whereby to update the pump for operation with syringes to be used with the syringe pump.

26 Claims, 11 Drawing Sheets

OTHER PUBLICATIONS

"Programmable Syringe Pumps", printed from www.jkem.com/psp.html captured by archive.org on Jun. 24, 2008.*

"Programmable Syringe Pump", J-KEM Scientific Inc., 2007.*

"The Univentor 864 Syringe Pump", Univentor product manual, 2005.*

Medfusion™ PharmGuard® Toolbox Medication Safety Software (Version 1.5.0) User's Manual, Smiths Medical, (82 pages).

Medfusion™ PharmGuard® Toolbox Medication Safety Software (Version 1.5.0) Administration Manual, Smiths Medical, (20 pages).

* cited by examiner

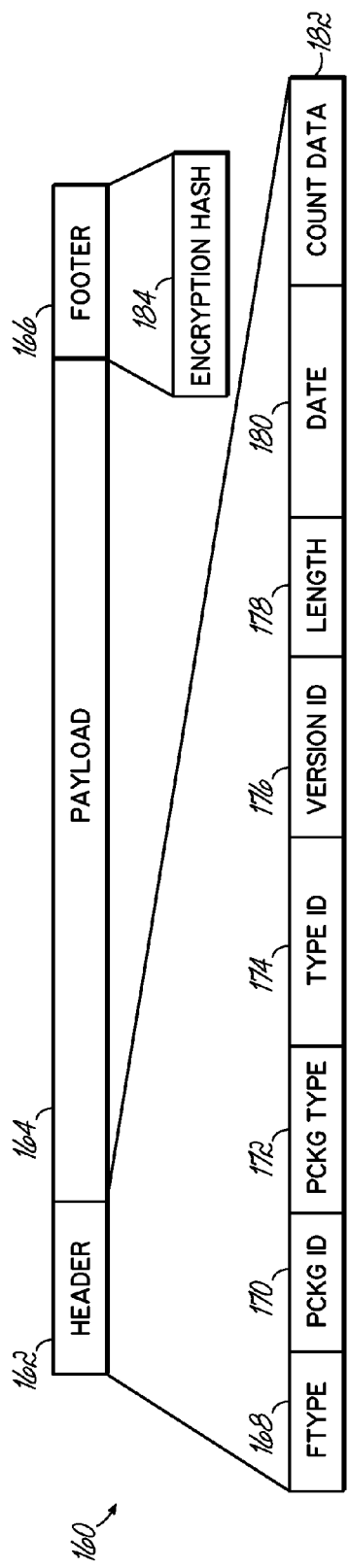
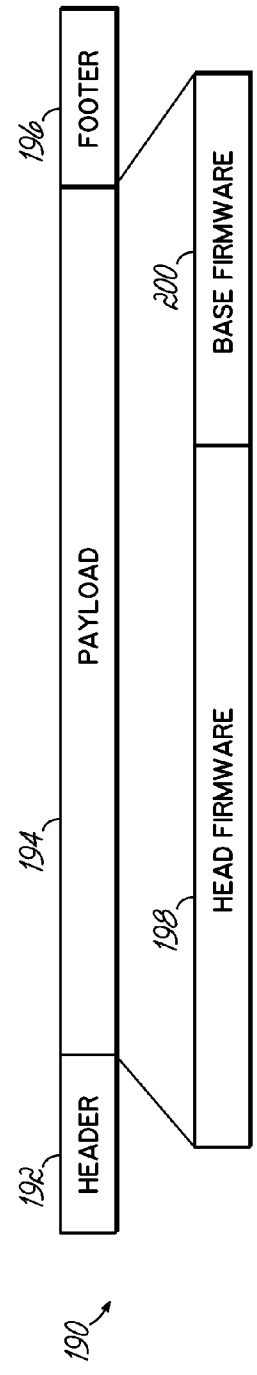
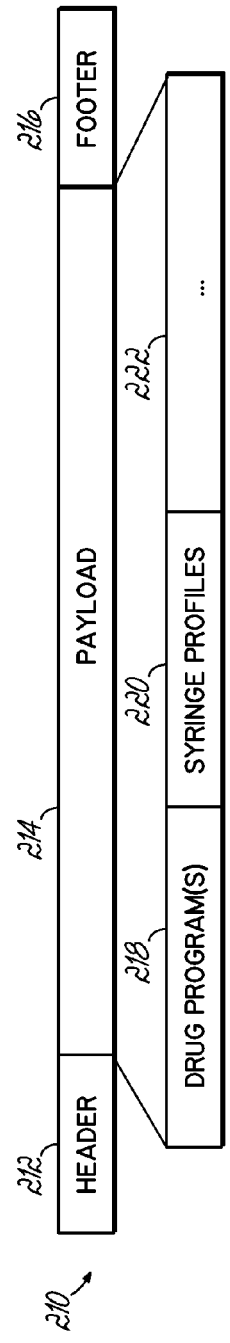
FIG. 6
FIG. 7A
FIG. 7B

UPDATING SYRINGE PROFILES FOR A SYRINGE PUMP

FIELD OF THE INVENTION

The present invention relates to drug infusion pumps, and more particularly to updating a memory thereof.

BACKGROUND OF THE INVENTION

The administration of many medications requires specific dosing regimens that occur over a relatively long period of time. To this end, the development of syringe pumps has dramatically benefited patients needing volumetrically proportioned delivery of their medication. Conventional syringe pumps generally comprise a housing upon which to mount a syringe. The syringe is typically filled with one or more chemical, nutritional or biological substances that are mixed into a uniform solution. A piston drive associated with the pump forces a plunger through the syringe. As the plunger travels through the syringe, the contents of the syringe are forced out into flexible tubing and/or catheters and into the patient.

Typically, the contents for syringes are mixed and the syringes filled by pharmacists at a facility. The pharmacists, in turn, select a syringe from among a small selection that can be used by the syringe pumps for that facility. In turn, the selection of syringes to use with syringe pumps is often programmed into those syringe pumps at the factory and static. Thus, conventional syringe pumps are configured to operate with only that small selection of syringes, and pharmacists within a facility are limited to those syringes. However, drug manufacturers have recently begun mixing their drugs at their facilities, and thus have begun to utilize their own custom syringes for containing their respective drugs. These custom syringes are often different from the selection of syringes that are used by a particular facility, and thus are often different from the syringes that can be used the syringe pumps for that facility as the syringe pumps do not contain data about the new syringes to use to infuse the contents thereof.

Consequently, there is a continuing need to update syringe pumps for operation with new syringes.

SUMMARY OF THE INVENTION

Embodiments of the invention provide a method and system to update a syringe pump for operation with a plurality of syringes to be used thereby. In particular, embodiments of the invention update syringe pumps of the type that are adapted to support a syringe having a plunger therein, a piston drive adapted to couple to the plunger, a processor operably coupled to control movement of the piston drive, and a memory adapted to store a plurality of syringe profiles for the plurality of syringes. Advantageously, each syringe profile contains data for use by the processor to control movement of the piston drive in relation to a respective syringe in order to expel fluid therefrom at a rate. To that end, and with a computing system containing a database of data correlated to an array of syringes for which the syringe pump could be used, a plurality of syringe profiles for the syringes to be used by the syringe pump in a facility or portion thereof are culled from the database. The memory of the syringe pump is then updated while in the facility with the culled plurality of syringe profiles whereby to update the syringe pump with operation with the syringes to be used with the syringe pump in the facility or portion thereof.

Alternative embodiments of the invention provide a method to update a syringe pump for operation with a plurality of syringes to be used thereby as well as a syringe pump configured to update the plurality of syringes it uses. In these alternative embodiments of the invention, the syringe pump includes a housing adapted to support a syringe having a plunger therein, a piston drive adapted to couple to the plunger, a processor operably coupled to control movement of the piston drive, and a memory adapted to store a plurality of syringe profiles for a plurality of different syringes to be used by the syringe pump within a facility or portion thereof. Again, each syringe profile contains data for use by the processor to control movement of the piston drive in relation to a respective syringe in order to expel fluid therefrom at a rate. However, the syringe pump receives a plurality of syringes for the syringes to be used by the syringe pump within the facility or portion thereof, the plurality of syringe profiles having been culled from a database of data correlated to an array of syringes for which the syringe pump could be used. The memory of the syringe pump is then updated with the culled plurality of syringe profiles whereby to update the syringe pump for operation with the syringes to be used with the syringe pump in the facility or portion thereof.

By virtue of the foregoing, there is thus provided methods, systems, and syringe pumps in which the syringes that could be used thereby are updated. These and other advantages will be apparent in light of the following figures and detailed description.

BRIEF DESCRIPTION OF THE DRAWINGS

The accompanying drawings, which are incorporated in and constitute a part of this specification, illustrate embodiments of the invention and, together with a general description of the invention given above and the detailed description of the embodiments given below, serve to explain the principles of the invention.

FIG. 6 is an illustration of the components of a configuration and/or firmware packages, including the sub-components of a header and footer thereof consistent with embodiments of the invention;

FIG. 7A is an illustration of the components of a firmware package, including the sub-components of the payload thereof consistent with embodiments of the invention;

FIG. 7B is an illustration of the components of a configuration package, including the sub-components of the payload thereof consistent with embodiments of the invention;

It should be understood that the appended drawings are not necessarily to scale, presenting a somewhat simplified representation of various features illustrative of the basic principles of embodiments of the invention. The specific design features of embodiments of the invention as disclosed herein, including, for example, specific dimensions, orientations, locations, and shapes of various illustrated components, as well as specific sequences of operations (e.g., including concurrent and/or sequential operations), will be determined in part by the particular intended application and use environment. Certain features of the illustrated embodiments may have been enlarged or distorted relative to others to facilitate visualization and clear understanding.

DETAILED DESCRIPTION

Hardware and Software Environment

Figure 1:
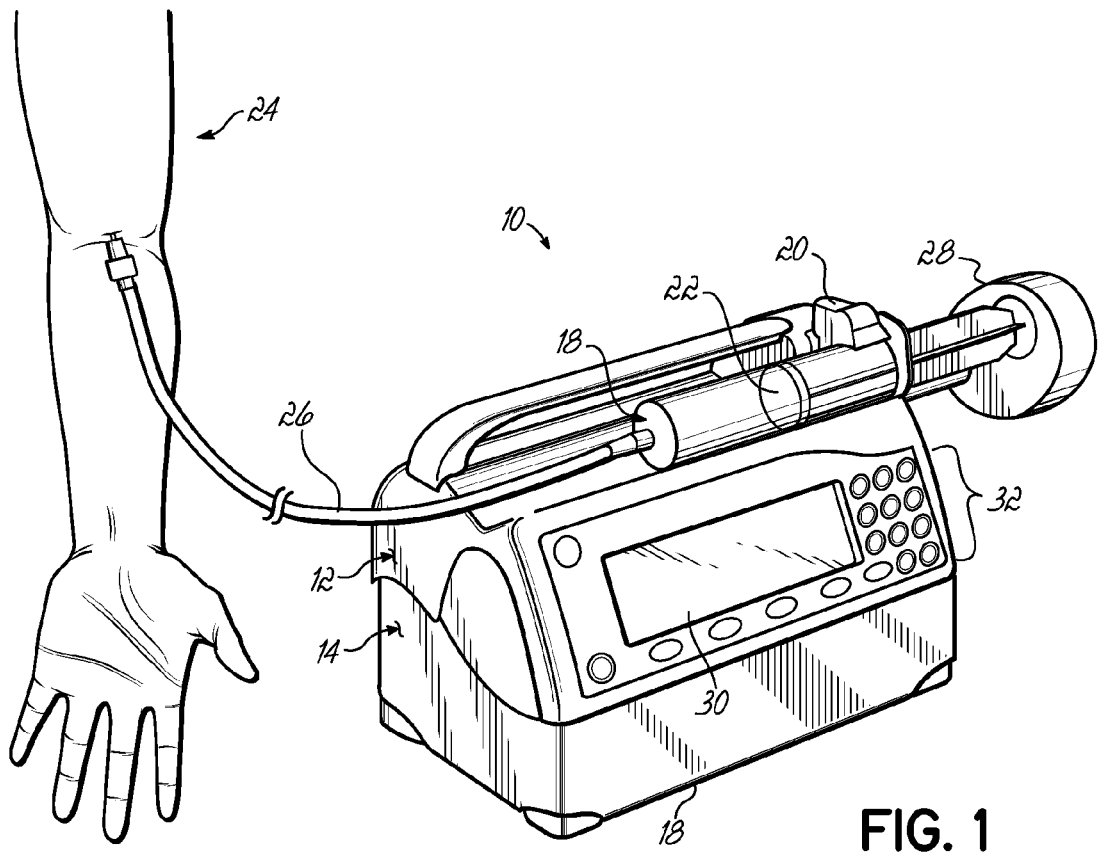
FIG. 1 is an illustration of a syringe pump consistent with embodiments of the invention.

Turning to the drawings, wherein like numbers denote like parts throughout the several views, FIG. 1 is an illustration of an exemplary syringe pump 10 consistent with embodiments of the invention. In particular, the pump 10 includes a head 12 and a base 14. As illustrated in FIG. 1, the pump 10 is configured to infuse the fluid contents of a pharmaceutical cartridge, or syringe 16, that in turn includes a housing 18 supported on the head 12 of the pump 10 and secured by a clamp 20. The clamp 20 is coupled to a sensor, which is typically internal to the head 12, to determine the outer diameter of the syringe 16. The syringe 16 includes a plunger 22 that regulates the flow of the fluid to a patient 24 via infusion line 26. That is, the plunger 22 comprises a piston-type mechanism that is internal to the housing 18 and is pushed to urge the fluid contents out of an outlet of the syringe 16 along the infusion line 26 to the patient 24.

To this end, a motor internal to the housing head 12 actuates a pusher, or piston drive 28, to move the plunger 22. A sensor (not shown), which is typically internal to the piston drive 28, monitors the force exerted by the piston drive 28 to determine the fluid force of the fluid upon the patient 24. The piston drive 28 drives the fluid of the syringe 16 into the downstream infusion line 26 at a controlled rate based upon a drug program associated with the contents of the syringe 16, a syringe profile that characterizes the physical characteristics of the syringe 16 and is used to identify the syringe 16, patient information (e.g., weight or body surface area), a desired rate at which to infuse the contents of the syringe 16 and/or additional operating parameters. The housing 18 of the syringe 16 is typically retained in such a way as to allow the plunger 22 to be pushed or pulled by the piston drive 28, but to prevent the plunger 22 from moving of its own accord as a result of siphoning of fluid from the syringe 16 or pressure in the infusion line 26. For instance, the housing 18 may be retained by means of a slot to hold at least a portion of the housing 18 while the plunger 22 may be retained by a forward facing surface of the piston drive 28 that clamps the base of the plunger 22 thereto.

As illustrated in FIG. 1, the head 12 includes a display 30 and a plurality of operator interface input mechanisms 32 (hereinafter, "operating interface" 32), such as a keyboard, switches, softkeys, actuators and/or other user interfaces. In some embodiments, the display 30 is responsive to user interaction therewith and may be a touch screen display. The display 30 may display options for a user to input with the operator interface 32. Such input may include selecting various menu items, including selecting various programs and/or profiles, as well as the input of data pertaining to infusion characteristics and/or other data related to the pump or operation thereof.

While generally not shown in FIG. 1, one that is skilled in the art will recognize that there may be additional infusion lines to the patient 24 and that the pump 10 may include additional valve mechanisms, clamps, caps, stopcocks, connectors and additional sensors as per system specifications.

Figure 2:
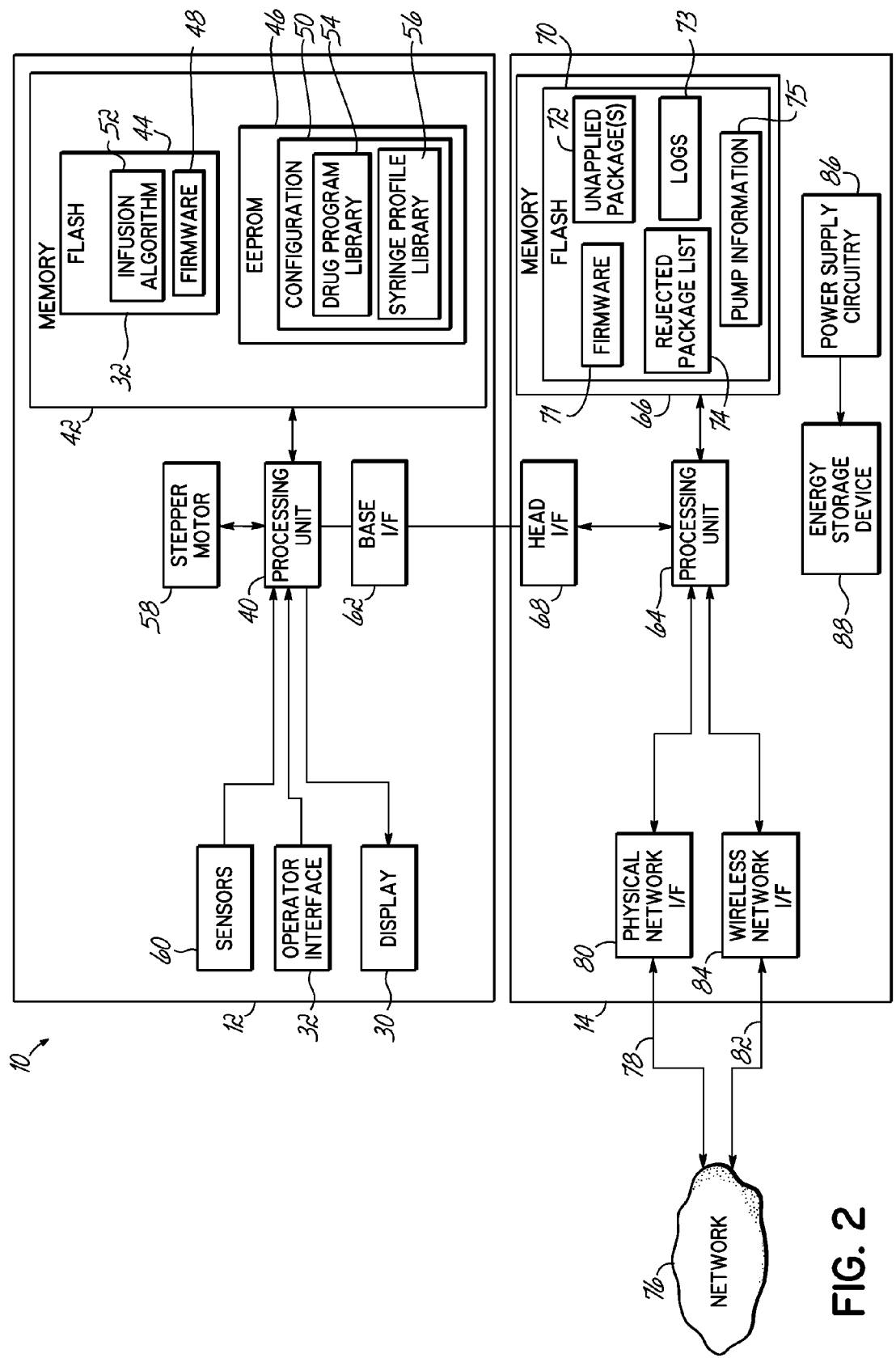
FIG. 2 is a diagrammatic illustration of the hardware and software components of the syringe pump of FIG. 1.

FIG. 2 illustrates a hardware and software environment for the pump 10, and particularly the head 12 and base 14 thereof. The head 12 includes at least one head processing unit 40 coupled to a head memory 42. Each head processing unit 40 is typically implemented in hardware using circuit logic disposed in one or more physical integrated circuit devices, or chips. Each head processing unit 40 may be one or more microprocessors, micro-controllers, field programmable gate arrays, or ASICs, while head memory 42 may include a plurality of types of memory, including a flash memory 44 and an electronically erasable programmable read-only memory 46 (illustrated as, and hereinafter, "EEPROM" 46). As such, head memory 42 may be considered to include memory storage physically located elsewhere in the head 12 (e.g., any cache memory in the at least one head processing unit 40, as well as flash memory 44, EEPROM 46, and any additional memory in the head 12). Similarly to each head processing unit 40, head memory 42, flash memory 44, and EEPROM 46 are also typically implemented using circuit logic disposed on one or more physical integrated circuit devices, or chips.

As illustrated in FIG. 2, the flash memory 44 is configured to contain firmware 48 for the head 12 while the EEPROM 46 is configured to contain configuration data 50. The firmware 48 includes data to control the components of the head 12 as well as an infusion algorithm 52. The infusion algorithm 52 is configured to be executed by the head processing unit 40 to determine a distance to move the plunger 22 of the syringe 16 over a time to achieve a desired rate of infusion. In particular, the distance-over-time to move the piston drive 28 to achieve a desired rate of infusion may be determined with respect to a drug program selected from at least one drug program library 54 in the configuration data 50, a syringe profile selected from at least one syringe profile library 56 in the configuration data 50 or a syringe profile from the at least one syringe profile library 56 otherwise associated with a selected drug program, data input by the user through the display 30 and/or operator interface 32 (e.g., patient weight, patient body-surface area, the rate of infusion), and/or additional infusion parameters. Upon determining the distance over the time, the head processing unit 40 is configured to operate a stepper motor 58 to control the piston drive 28 coupled to the stepper motor 58 in a manner consistent with the determined distance-over-time.

In some embodiments, each drug program is associated with custom infusion parameters which contain specific information about modes of operation used in the pump 10, that are associated with specific syringe profiles, and that are used by the head processing unit 40 to determine how to operate the stepper motor 58 and piston drive 28 to infuse the fluid contents of the syringe 16. For example, a drug program may include a name that specifies the particular fluid that is to be infused by that drug program, the particular syringe profile to use with that drug program, as well as the mode of infusion to use for that particular fluid. The modes of infusion may include a continuous mode (a continuous infusion of a specific flow rate in ml/hr with regard to volume limits, loading dose or bolus dose, the bolus dose being an optional parameter to specify a bolus volume to be delivered over a specified time, the loading dose being an optional parameter to use a specified volume as a one-time-only bolus prior to the start of normal delivery, and the volume limit being an optional parameter in which the pump stops or enters a "Keep Vein Open" rate once a specified volume has been reached), a mass mode (a continuous infusion mode programmed through drug concentration or dose rate in mass/hr with regard to volume limit, loading dose or bolus dose), a body weight infusion mode (that may be programmed by drug concentration, patient weight or drug dosage, in which the pump calculates the correct flow rate in ml/hr to achieve a specified drug dose with regard to volume limit, loading dose or bolus dose), a volume-over-time infusion mode (in which the pump calculates the flow rate for a dose volume over a delivery time in ml/hr without regard to volume limit, loading dose or bolus dose), an intermittent volume-over-time mode (in which the clinician specifies a delivery volume for a specific delivery time, after which the delivery stops for a programmed interval, with the pattern repeating without regard to volume limit, loading dose or bolus dose), and a custom dilution mode (in which the patient's weight, initial drug concentration, target dose rate and target volume rate are entered, followed by the pump calculating the amount of fluid required to dilute the initial drug concentration, the actual dose rate and the actual total volume).

Each syringe profile, on the other hand, contains characterization information (about a syringe e.g., physical measurements of the syringe) and/or identification information that is used by the head processing unit 40 to determine how to operate the stepper motor 58 and piston drive 28 to infuse the fluid contents of the syringe 16. For example, a syringe profile may include a model name that specifies the particular model and/or manufacturer of a syringe 16 that is to be used, as well as a specific volume for that syringe 16 and physical measurements associated with the syringe 16. In some embodiments, each syringe profile also includes information that is utilized to display an identification of a syringe 16 (e.g., the manufacturer and model of a syringe 16) on the display 30 of the pump 10 and is further utilized by the pump 10 to calculate and/or determine, during an infusion, when the syringe 16 is empty.

The head processing unit 40 is further coupled to the display 30 as well as the operator interface 32. The head processing unit 40 is also coupled to a plurality of sensors 60. For example, the plurality of sensors 60 may include a force transducer sensor (not shown) to indicate the force exerted on the plunger 22 of a syringe 16, a syringe plunger loaded sensor (not shown) to indicate that the plunger 22 of the syringe 16 is loaded on the piston drive 28, a plunger travel sensor (not shown) to indicate the distance traveled by the plunger 22 of the syringe 16, a syringe size sensor (not shown) coupled to the clamp 20 to indicate the size of the syringe 16, and a motor rotation sensor (not shown) to indicate rotation of the stepper motor 58 and the amount thereof. The head processing unit 40 is coupled to a base interface 62 (illustrated as "base I/F" 62) to interface with the base 14.

Turning to the base, the base 14 includes at least one base processing unit 64 coupled to a base memory 66 and a head interface 68 to interface with the base interface 62 of the head 12. Each base processing unit 64 is also typically implemented in hardware using circuit logic disposed in one or more physical integrated circuit devices, or chips. Each base processing unit 64 may also be one or more microprocessors, micro-controllers, field programmable gate arrays, or ASICs, while base memory 66 includes a flash memory 70, and is also typically implemented using circuit logic disposed on one or more physical integrated circuit devices, or chips. It will be appreciated by a person having ordinary skill in the art that base memory 66 may be considered to include memory storage physically located elsewhere in the base 14 (e.g., any cache memory in the at least one base processing unit 64 and any additional memory in the base 14). The flash memory 70 is configured to store the firmware 71 for the base 14 as well as any unapplied packages in an unapplied packages section 72 to apply to the firmware and/or configuration of the pump 10. In some embodiments, the unapplied packages section 72 includes separate sections for firmware and configuration packages, and, in more specific embodiments, the separate section for firmware packages includes a first section for new firmware for the head 12 of the pump 10 and a second section for new firmware for the base 14 of the pump 10. The flash memory 70 is further configured to store a log 73 that stores all data generated by the head 12 and base 14, a rejected package list 74 that lists all packages that have previously been considered for download by the base 14 but nevertheless rejected, and a pump information data structure 75. The pump information section 75 is configured to store information about the pump 10 that is, in turn, used to determine whether to download a configuration and/or firmware package. In specific embodiments, the pump information section 75 includes an indication of the particular revision of each package installed on the pump 10 (whether configuration and/or firmware), a data structure identifier for the pump 10 that indicates the particular data structure used by the pump 10 to store information, and a component identifier that indicates the particular hardware configuration of the pump 10. With respect to the data structure identifier, the data structure refers to the particular method of storing and organizing data in the pump 10. As such, the data structure identifier is a particular identifier for the data structure used by the pump 10. In this manner, a configuration package is only downloaded when the data structure identifier of that configuration package matches the data structure identifier of a respective pump 10 to ensure compatibility of configuration data of the configuration package with the data structure of the pump 10. The component identifier, on the other hand, is an identifier used to indicate the particular version of hardware configuration of the pump 10. For example, if a first version of a pump 10 has a different wireless network IF 84 than a second version of a pump 10, a component identifier of the first version of the pump 10 will have at least one different value than a component identifier for the second version of the pump 10. In this manner, a firmware package is only downloaded when a hardware configuration identifier of that configuration package matches the component identifier of a respective pump 10 to ensure compatibility of the firmware of the firmware package with the particular hardware of the pump 10.

In some embodiments, the base 14 is configured to couple to a network 76 through a cable as at 78 with a wired network interface 80 (illustrated as "wired network I/F" 80) coupled to the base processing unit 64. In alternative embodiments, the base 14 is configured to couple to the network 76 through a wireless signal as at 82 with a wireless network interface 84 (illustrated as "wireless network I/F" 84) coupled to the base processing unit 64. In this manner, the base 14 is configured to communicate across the network 76 to send and receive data, as well as to receive at least one new package and store in the unapplied packages section 72. The base 14 also includes power supply circuitry 86 to convert AC power to DC power for the head 12 and base 14 when the base 14 is coupled to an AC power source (not shown), as well as an energy storage device 88 to supply DC power to the head 12 and base 14 when the base 14 is not coupled to the AC power source.

Thus, in some embodiments, the pump 10 is a syringe pump such as the Medfusion® 3500 V.5 Syringe Pump or the Medfusion® 4000 Syringe Pump, both of which are distributed by Smiths Medical of St. Paul, Minn.

Figure 3:
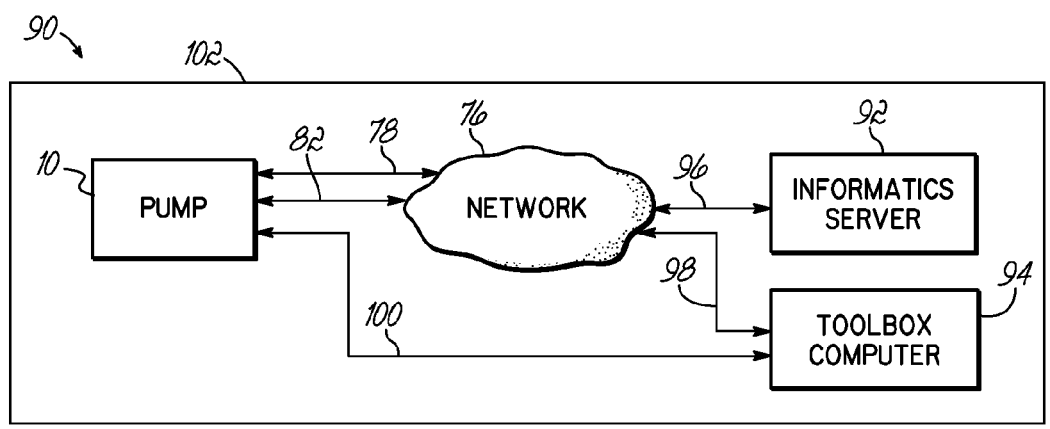
FIG. 3 is a diagrammatic illustration of various forms of communicatively coupling the syringe pump of FIG. 1 with a server and/or computer.

FIG. 3 is a diagrammatic illustration 90 of the connection of the pump 10 to at least one server 92 and/or at least one computer 94 consistent with embodiments of the invention. In some embodiments, the server 92 includes a medical device server (hereinafter, an "MDS") that is configured to receive and process data from the pump 10 and/or a package server to manage configuration and/or firmware packages for the pump 10. Thus, the informatics server 92 is coupled to the network 76 as at 96 to communicate with the pump 10. In specific embodiments, the server 92 is referred to as an Informatics Server. The computer 94, on the other hand, is configured to develop configuration and/or firmware packages for the pump 10. In some embodiments, the computer 94 is coupled to the network 76 as at 98 and configured to provide packages to the server 92. In alternative embodiments, the computer 94 is coupled directly with the pump 10 as at 100 and configured to provide packages directly to the pump 10 and/or retrieve data therefrom. In specific embodiments, the computer 94 is referred to as a Toolbox computer. In some embodiments, the pump 10, server 92, and/or computer 94 (and, though not shown in FIG. 3, the patient 24) are located in a facility 102, such as a hospital or medical treatment facility.

Figure 4:
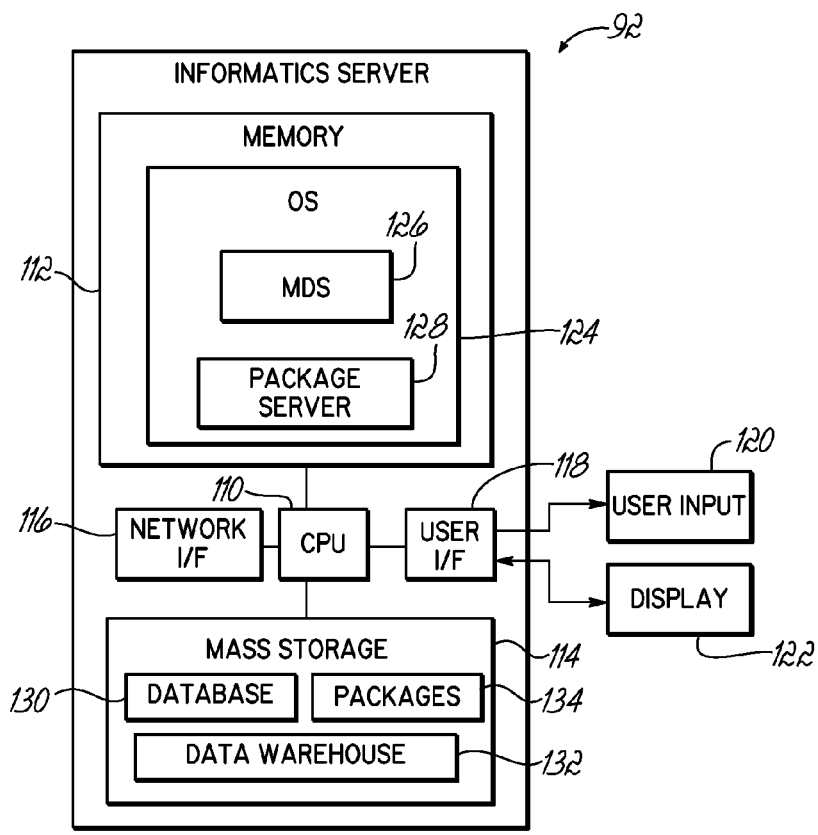
FIG. 4 is a diagrammatic illustration of the hardware and software components of the server of FIG. 3.

FIG. 4 is a diagrammatic illustration of the server 92 consistent with embodiments of the invention. The server 92, in specific embodiments, may be at least one computer, computer system, computing device, server, disk array, or programmable device such as a multi-user computer, a single-user computer, a handheld device, a networked device (including a computer in a cluster configuration), etc. The server 92 includes at least one central processing unit ("CPU") 110 coupled to a memory 112. Each CPU 110 is typically implemented in hardware using circuit logic disposed in one or more physical integrated circuit devices, or chips and may be one or more microprocessors, micro-controllers, field programmable gate arrays, or ASICs, while memory 112 may include random access memory (RAM), dynamic random access memory (DRAM), static random access memory (SRAM), flash memory, EEPROM and/or another digital storage medium, and is typically implemented using circuit logic disposed on one or more physical integrated circuit devices, or chips. As such, memory 112 may be considered to include memory storage physically located elsewhere in the Informatics server 92, e.g., any cache memory in the at least one CPU 110, as well as any storage capacity used as a virtual memory, e.g., as stored on a mass storage device 114, a computer, or another controller coupled to the server 92 through at least one network interface 116 by way of the network 76 (not shown in FIG. 4).

In some embodiments, the server 92 includes peripheral devices coupled through an input/output device interface 118. In particular, the server 92 is configured to receive data from a user through at least one user interface (including, for example, a keyboard, mouse, and/or other user interface) 120 and/or output data to a user through at least one output device (including, for example, a display, speakers, and/or another output device) 122. Moreover, in some embodiments, the input/output device interface 118 communicates with a device that includes a user interface and at least one output device in combination, such as a touchscreen (not shown).

The server 92 is under the control of an operating system 124 and executes or otherwise relies upon various computer software applications, components, programs, files, objects, modules, etc., consistent with embodiments of the invention. In particular, the server 92 is configured with an MDS software component 126 and a package server software component 128. Moreover, the server 92 is configured with a database 130 to store information from syringe pumps, a data warehouse data structure 132 that provides a static copy of at least some of the data of the database 130 and is typically updated once a day, and a packages data structure 134 to store available packages to be sent to syringe pumps.

In some embodiments, the MDS software component 126 (or, more simply, "MDS" 126) is configured to receive data from the pump 10, determine the validity of the pump 10, determine the validity of data from the pump 10, store that data, and respond with an acknowledgment that the MDS 126 has verified and received the data. The MDS 126 is also configured to notify the pump 10 of available configuration and/or firmware packages available to replace the respective configuration data and/or firmware packages already configured upon the pump 10. In some embodiments, the MDS 126 notifies the pump 10 of available packages (e.g., configuration and/or firmware packages) that have not previously been applied (e.g., not previously installed by the pump 10), while in alternative embodiments the MDS 126 notifies the pump 10 of any packages that are stored in the packages data structure 134 on the server 92 regardless of whether or not they have been previously installed by the pump 10.

The package server software component 128 is configured to provide information about configuration and/or firmware packages in response to a request from the pump 10 for that information, as well as a configuration or firmware package in response to a request from the pump 10 for that particular package. The package server software component 128 is further configured to assign unique identifiers to each package. Moreover, in some embodiments, the package server software component 128 is configured to control the availability of packages. For example, a user may wish to stop one or more packages from being made available. However, the user may not wish to remove those packages completely. Thus, the user may selectively disable the available of one or more packages with the package server software component 128 such that information about the one or more packages is not sent to the pump 10 (e.g., including their unique identifier) and such that those one or more packages cannot be downloaded by the pump 10.

Figure 5:
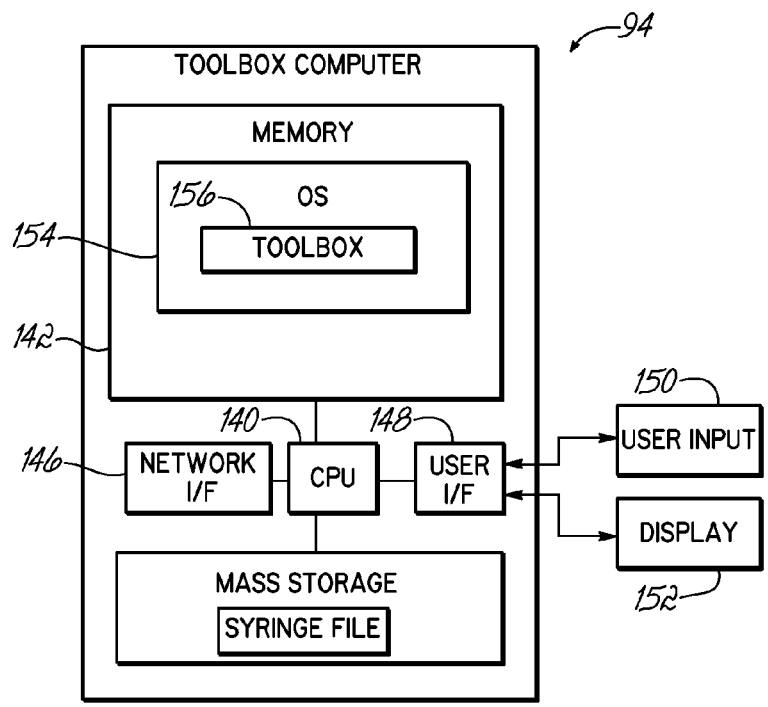
FIG. 5 is a diagrammatic illustration of the hardware and software components of the computer of FIG. 3.

FIG. 5 is a diagrammatic illustration of the computer 94 consistent with embodiments of the invention. The computer 94, similarly to the server 92, may be at least one computer, computer system, computing device, server, disk array, or programmable device such as a multi-user computer, a single-user computer, a handheld device, a networked device (including a computer in a cluster configuration), etc. Also, and similarly to the server 92, the computer 94 includes at least one CPU 140 coupled to a memory 142. Each CPU 140 is typically implemented in hardware using circuit logic disposed in one or more physical integrated circuit devices, or chips and may be one or more microprocessors, micro-controllers, field programmable gate arrays, or ASICs, while memory 142 may include RAM, DRAM, SRAM, flash memory, and/or another digital storage medium, and is also typically implemented using circuit logic disposed on one or more physical integrated circuit devices, or chips. As such, memory 142 may be considered to include memory storage physically located elsewhere in the computer 94, e.g., any cache memory in the at least one CPU 140, as well as any storage capacity used as a virtual memory, e.g., as stored on a mass storage device 144, a computer, or another controller coupled to the computer 94 through at least one network interface 146 by the network 76 (not shown in FIG. 5).

In some embodiments, the computer 94 includes peripheral devices coupled through an input/output device interface 148. In particular, the computer 94 is configured to receive data from the user through at least one user interface (including, for example, a keyboard, mouse, and/or other user interface) 150 and/or output data to a user through at least one output device (including, for example, a display, speakers, and/or another output device) 152. Moreover, in some embodiments, the input/output device interface 148 communicates with a device that includes a user interface and at least one output device in combination, such as a touchscreen (not shown).

The computer 94 is under the control of an operating system 154 and executes or otherwise relies upon various computer software applications, components, programs, files, objects, modules, etc., consistent with embodiments of the invention. In particular, the computer 94 is configured with a Toolbox software component 156. In some embodiments, the Toolbox software component 156 (or, more simply, "Toolbox" 156) is configured to receive a syringe file that contains a database of data correlated to an array of syringes that can be used by the pump 10 and determine, from user interaction with the Toolbox 156, which syringe profiles have been selected by a user to include in a configuration package for the pump 10. The Toolbox 156 is also utilized to download data directly from a pump 10 (e.g., from the log 73 of the pump 10) as well as provide packages directly to the pump 10 (e.g., for testing purposes) when the computer 94 is connected to the pump 10 directly (as at 100 in FIG. 3).

FIG. 6 is a diagrammatic illustration of generic components of a package 160 (e.g., a configuration or firmware package) that is developed by the computer 94 and utilized to update a pump 10. In particular, each package 160 includes a header 162, a payload 164, and a footer 166. The header 162 includes a number of fields that indicate information about the package 160. In some embodiments, the header 162 includes the following: a file type field 168 (illustrated as "FTYPE" 168) that indicates that the package 160 is of a package file-type; a package identification field 170 (illustrated as "PCKG ID" 170) that indicates a unique identification for the package 160; a package type field 172 (illustrated as "PCKG TYPE" 172) that indicates whether the package 160 is a firmware package or a configuration package; a type identification field 174 (illustrated as "TYPE ID" 174) that indicates the device for which that package 160 is intended; a version identification field 176 (illustrated as "VERSION ID" 176) that indicates either the data structure of a pump 10 for which the package 160 is configured or the hardware configuration of a pump 10 for which the package 160 is configured; a length field 178 (illustrated as "LENGTH" 178) that indicates the length of the payload 164 when it is encrypted, the length of the payload 164 when it is unencrypted, and/or the length of vendor data appended at the end of the header 162; a creation date field 180 (illustrated as "DATE" 180) that indicates the date and time the package 160 was created; and a drug program count data field 182 (illustrated as "COUNT DATA" 182) that indicates the number of bytes necessary to store a drug usage count for each drug program of a configuration package (e.g., the pump 10 is configured to count the number of times each drug program is selected for an infusion, thus the drug program count data field 182 indicates, for each drug program of a configuration package, the number of bytes necessary to maintain the count associated therewith). In some embodiments, the unique identification for the package 160 in the package identification field 170 includes a revision identifier of the package 160. In particular, this revision identifier indicates the particular revision of the data within the package (e.g., 1.0, 2.0, 2.0.1.0, 2.1). The footer 166, on the other hand, includes an encryption hash 184 that may be used to decrypt the payload 164. In some embodiments, the footer 166 includes a Secure Hash Algorithm ("SHA") hash, and in specific embodiments an SHA-1 hash. It will be appreciated by a person having ordinary skill in the art that the footer 166 may include alternative encryption hashes that correspond to alternative encryption methodologies used to encrypt the payload 164. Further alternatively, it will be appreciated by a person having ordinary skill in the art that the footer 166 may not include an encryption hash 184 when the payload 164 is not encrypted such that, in those embodiments, the footer 166 includes null data.

FIG. 7A is a diagrammatic illustration of payload components of a firmware package 190 consistent with embodiments of the invention. Similarly to FIG. 6, the firmware package 190 of FIG. 7A includes a header 192, a payload 194, and a footer 196. In some embodiments, the header 192 of the firmware package 190 of FIG. 7A includes the same respective fields as the header 162 specified in FIG. 6 (e.g., fields 168-182) with the exception that data in the version identification field 176 includes a hardware identifier that indicates which hardware configuration of a pump 10 the firmware package 190 is configured for. In some embodiments, data in the drug program count data field 182 of a firmware package 190 is null, as there are no drug programs contained in the payload 194. The footer 196 of the firmware package 190 of FIG. 7A includes the same encryption hash 184 as the footer 196 specified in FIG. 6. The payload 194 of the firmware package 190, on the other hand, includes the head firmware 198 and base firmware 200 for the pump 10.

FIG. 7B is a diagrammatic illustration of components of a configuration package 210 consistent with embodiments of the invention. Similarly to FIG. 6, the configuration package 210 of FIG. 7B includes a header 212, a payload 214, and a footer 216. In some embodiments, the header 212 of the firmware package 210 of FIG. 7B includes the same respective fields as the header 162 specified in FIG. 6 (e.g., fields 168-182), with the exception that data in the version identification field 176 includes a data structure identifier that indicates which data structure of a pump 10 the configuration package 210 is configured for. In some embodiments, the footer 216 of the configuration package 210 of FIG. 7B includes the same encryption hash 184 as the footer 196 specified in FIG. 6. The payload 214 of the configuration package 210, in turn, includes at least one drug program 218, at least one syringe profile 220, and additional operating parameters 222 for the pump 10. In some embodiments, the payload 214 of the configuration package 210 includes a plurality of drug programs 218, a plurality of syringe profiles 220 associated therewith, as well as additional operating parameters 222 for the pump 10.

A person having ordinary skill in the art will recognize that the environments illustrated in FIGS. 1-6, 7A and 7B are not intended to limit the scope of embodiments of the invention. In particular, the pump 10, server 92, and computer 94 may include additional components consistent with alternative embodiments of the invention. Indeed, a person having skill in the art will recognize that other alternative hardware and/or software environments may be used without departing from the scope of the invention. For example, the memory 42 of the head 12 and the memory 66 of the base 14 may include additional and/or alternative types of memory (e.g., RAM, DRAM, and SRAM) to those specified. Moreover, the MDS 126 and package server software component 128 may be configured on separate servers consistent with embodiments of the invention. Additionally, a person having ordinary skill in the art will appreciate that the pump 10, server 92, and computer 94 may include more or fewer applications disposed therein. As such, other alternative hardware environments may be used without departing from the scope of embodiments of the invention.

The routines executed to implement the embodiments of the invention, whether implemented as part of an operating system or a specific application, component, program, object, module or sequence of instructions executed by one or more pumps and/or computing systems will be referred to herein as a "sequence of operations," a "program product," or, more simply, "program code." The program code typically comprises one or more instructions that are resident at various times in various memory and storage devices, and that, when read and executed by one or more processors of a pump and/or computing system, cause that pump and/or computing system to perform the steps necessary to execute steps, elements, and/or blocks embodying the various aspects of the invention.

While the invention has and hereinafter will be described in the context of fully functioning pumps and/or computing systems, a person skilled in the art will appreciate that the various embodiments of the invention are capable of being distributed as a program product in a variety of forms, and that the invention applies equally regardless of the particular type of computer readable signal bearing media used to actually carry out the distribution. Examples of computer readable signal bearing media include but are not limited to physical and tangible recordable type media such as volatile and non-volatile memory devices, floppy and other removable disks, hard disk drives, optical disks (e.g., CD-ROM's, DVD's, etc.), among others, and transmission type media such as digital and analog communication links.

In addition, various program code described hereinafter may be identified based upon the application or software component within which it is implemented in a specific embodiment of the invention. However, it should be appreciated that any particular program nomenclature that follows is used merely for convenience, and thus the invention should not be limited to use solely in any specific application identified and/or implied by such nomenclature. Furthermore, given the typically endless number of manners in which computer programs may be organized into routines, procedures, methods, modules, objects, and the like, as well as the various manners in which program functionality may be allocated among various software layers that are resident within a typical computer (e.g., operating systems, libraries, APIs, applications, applets, etc.), it should be appreciated that the invention is not limited to the specific organization and allocation of program functionality described herein.

Software Description and Flows

Figure 8:
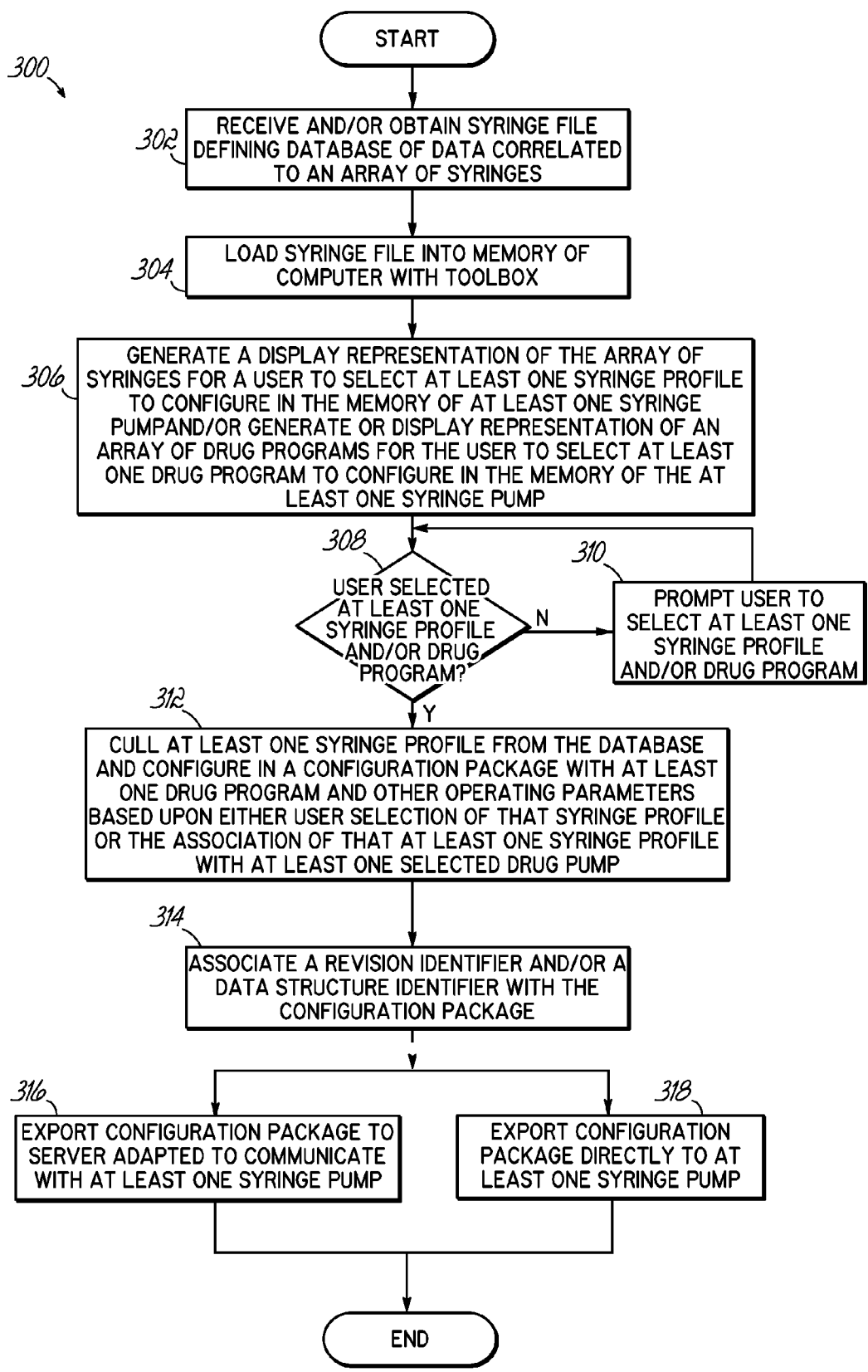
FIG. 8 is a flowchart illustrating a sequence of operations executable by the computer of FIG. 5 to configure at least one syringe profile into a configuration package.

FIG. 8 is a flowchart 300 illustrating a sequence of operations for a computer, and in particular for Toolbox program code configured thereupon, to configure at least one syringe profile in a configuration package consistent with embodiments of the invention. In particular, a syringe file defining a database of data correlated an array of syringes that may be used by a syringe pump is obtained and/or received by the computer (block 302). In some embodiments, the syringe file is obtained from a manufacturer of the syringe pump. In alternative embodiments, the syringe file is obtained from a third party, included in a program product, included in a computing system (e.g., including the computer executing the sequence of operations of FIG. 8), received across a network, received from a portable memory device, and/or otherwise obtained. Despite the manner of obtaining and/or receiving the syringe file, the syringe file is loaded into the memory of the computer (block 304). A display representation of the array of syringes is then provided for a user to select at least one syringe profile to configure in a memory a pump (block 306). In specific embodiments, a list of the array of syringes is displayed from which the user selects at least one syringe profile, and typically a plurality of syringe profiles, to be used by the pump. In additional and/or alternative embodiments, a display representation of an array of drug programs is provided for the user to select at least one drug program to configure in the memory of the pump (block 306). In specific additional and/or alternative embodiments, a list of the array of drug programs is displayed from which the user selects at least one drug program, and typically a plurality of drug programs, to be used by the pump. When it is determined that the user has not selected at least one syringe profile and/or that the user has not selected at least one drug program ("No" branch of decision block 308), the user is prompted to select at least one syringe profile and/or at least one drug program (block 310).

When it is determined that the user has selected at least one syringe profile ("Yes" branch of decision block 308), the at least one selected syringe profile is culled from the database of the plurality of syringe profiles and configured in a configuration package for the pump, the configuration package additionally including at least one drug program and other operating parameters for the pump to calculate the movements of a piston drive to infuse fluid contents of a syringe at a selected rate of infusion (block 312). Additionally and/or alternatively, when it is determined that the user has selected at least one drug program ("Yes" branch of decision block 308), at least one syringe profile is culled from the database of the plurality of syringe profiles and configured in the configuration package for the pump based upon the selection of at least one drug program with which that syringe profile is associated (block 312). Thus, when a drug program is associated with a specific syringe, the syringe profile associated with that specific syringe is included in the syringe profiles to configure with pumps that use that particular drug program. As such, upon selection of a drug program at the pump, the syringe profiles associated therewith may be selectively displayed. Returning to FIG. 8, a revision identifier (to identify the particular revision number of the configuration package) and/or a data structure identifier (to identify the data structure of the pump for which the configuration package is intended) are associated with the configuration package (block 314). After associating the configuration package with the revision identifier and data structure identifier (block 314), the configuration package may be either exported to a server adapted to communicate that package to the pump over a network (block 316) or exported directly to the pump (block 318). Thus, in this manner, the configuration package may be exported en masse to a plurality of pumps from a central location (e.g., the server) or exported directly to at least one pump.

Figure 9:
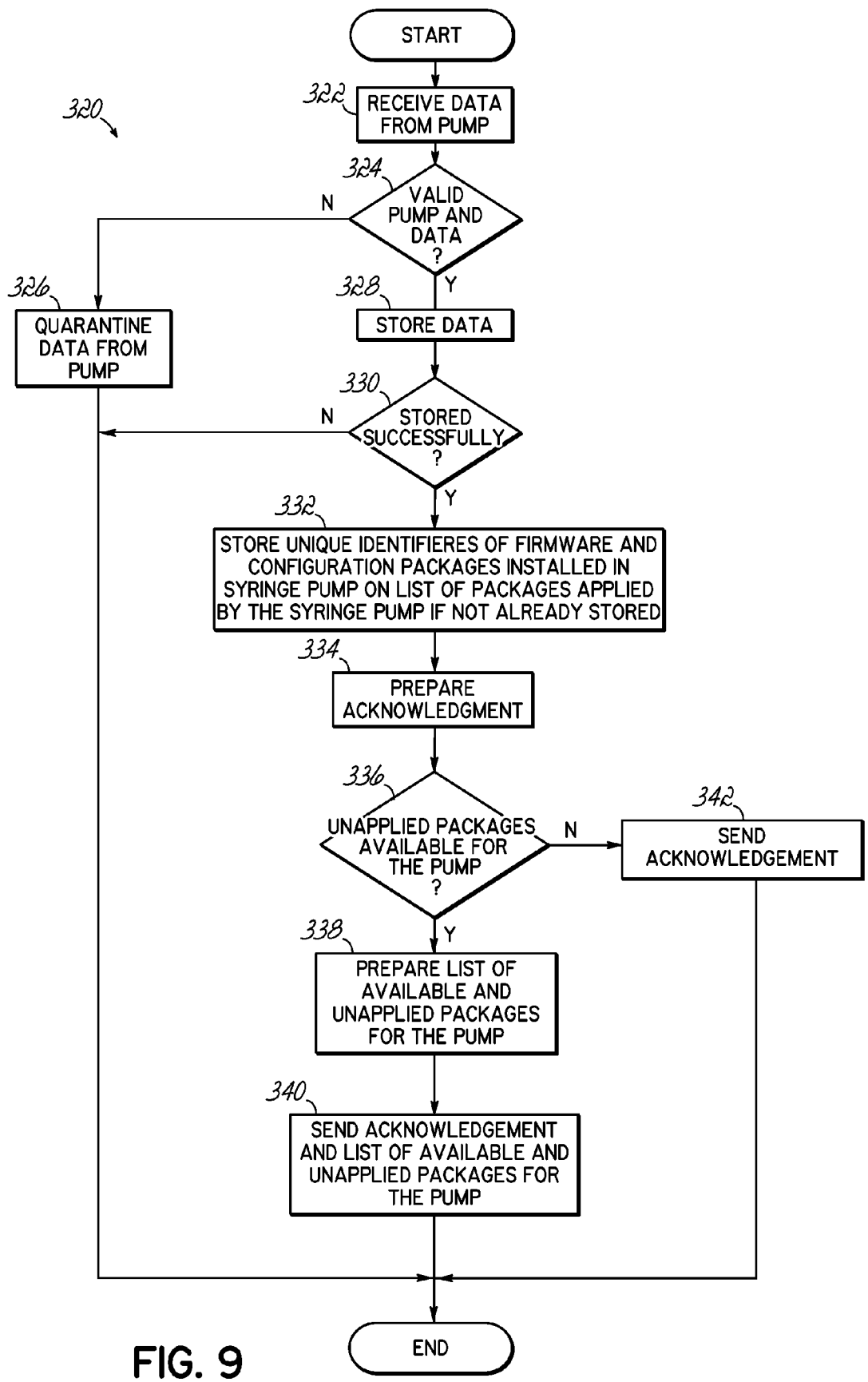
FIG. 9 is a flowchart illustrating one embodiment of a sequence of operations executable by the server of FIG. 4 to acknowledge events from, and send data about available packages to, the pump of FIG. 1.

FIG. 9 is a flowchart 320 illustrating one embodiment of a sequence of operations for a server, and in particular for MDS program code configured thereupon, to receive and store data from a pump as well as notify the pump of available packages consistent with embodiments of the invention. In response to receiving data from the pump (block 322) the MDS determines whether the pump that sent the data is a valid pump and whether the data is valid data (block 324). In some embodiments, the MDS determines whether a pump is a valid pump by determining whether a type identifier associated with a pump message indicates that the message is from a pump, and in particular a Medfusion 4000 syringe pump. When the pump is not a valid pump (e.g., the type identifier of the pump does not match known a known type identifier of a pump) and/or when the data from the pump is corrupted or otherwise incomplete (e.g., a data field that is supposed to be included by the pump is not included, or data from the pump is in an incorrect format, damaged, or otherwise has an error) ("No" branch of decision block 324) the data from the pump is quarantined (block 326). Data that is quarantined is stored in a separate location than valid data from valid pumps. However, users may review quarantined data to determine if there is a fault with particular pumps, communications errors associated with particular pumps, and/or other faults that occurred with the pumps and/or server that resulted in quarantined data. When the pump is a valid pump and when the data from the pump is valid data ("Yes" branch of decision block 324) that data is stored (block 328) and the MDS subsequently determines whether the data has been stored successfully (block 330). When the data is not stored successfully ("No" branch of decision block 330) the sequence of operations of FIG. 9 ends.

When data from a pump is stored successfully by the MDS ("Yes" branch of decision block 330), the MDS stores, in a database, the unique identifiers of firmware and configuration packages installed on the pump that are included with the data from the pump, if the database does not already include those identifiers (block 332). The MDS then prepares an acknowledgment for the pump that indicates that the MDS has stored the data successfully (block 334). The MDS then determines whether there are unapplied packages available for the pump (block 336).

In some embodiments, the MDS determines, from its memory, whether there are any available packages (firmware and/or configuration) for pump. Alternatively, the MDS determines, from communication with a package server software component, whether there are any packages available for the pump. The MDS also determines, based on a list of packages applied by the pump and the serial number of the pump, whether any available packages have previously been applied by the pump. When there are available and unapplied packages for the pump ("Yes" branch of decision block 336), the MDS prepares a list of all those unapplied and available packages to send to the pump (block 338). The MDS then sends, to the pump, the acknowledgment that it has successfully stored data from the pump along with the list of all unapplied and available packages for the pump (block 340). In some embodiments, this list indicates a unique identifier for each of the unapplied and available packages. Returning to block 336, when there are no available and unapplied packages for the pump ("No" branch of decision block 336), the MDS sends the acknowledgment that it has stored the data from the pump successfully (block 342).

After the MDS quarantines data from the pump (block 326), after the MDS sends the acknowledgement as well as a list of available and unapplied packages to the pump (block 340), or after the MDS sends the acknowledgment only (block 342), the sequence of operations of FIG. 9 ends.

Figure 10:
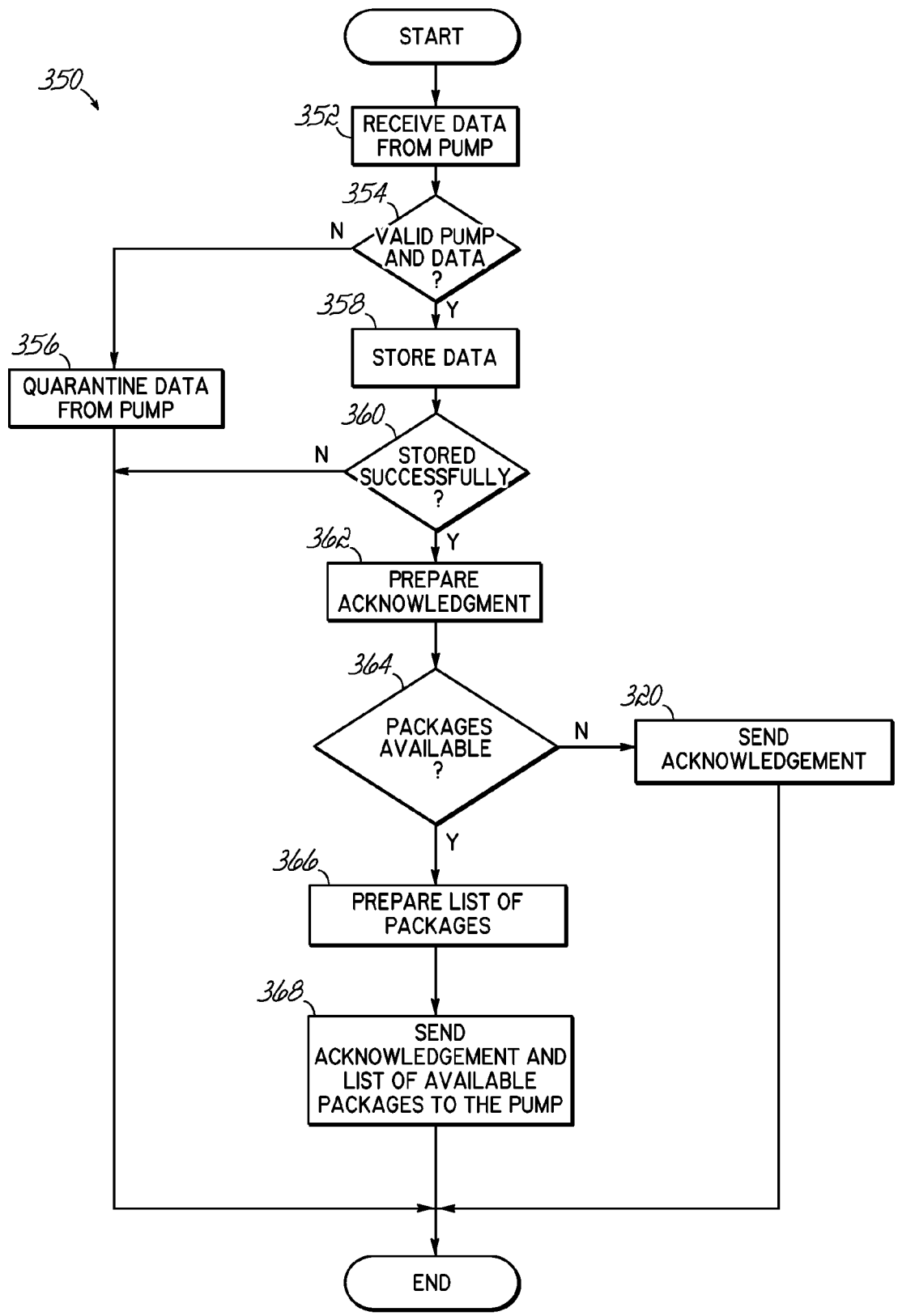
FIG. 10 is a flowchart illustrating an alternative embodiment of a sequence of operations executable by the server of FIG. 4 to acknowledge events from, and send data about available packages to, the pump of FIG. 1.

FIG. 10 is a flowchart 350 illustrating an alternative embodiment of a sequence of operations for a server, and in particular for MDS program code configured thereupon, to receive and store data from a pump as well as notify the pump of available packages consistent with embodiments of the invention. Similarly to the sequence of operations in FIG. 9, the sequence of operations of FIG. 10 illustrates that, in response to receiving data from the pump (block 352) the MDS determines whether the pump that sent the data is a valid pump and whether the data is valid data (block 354). When the pump is not a valid pump and/or when the data from the pump is corrupted or otherwise incomplete ("No" branch of decision block 354) the data from the pump is quarantined (block 356). When the pump is a valid pump and when the data from the pump is valid data ("Yes" branch of decision block 354) that data is stored (block 358) and the MDS subsequently determines whether the data has been stored successfully (block 360). When the data has not been stored successfully ("No" branch of decision block 360) the sequence of operations of FIG. 10 ends.

Unlike the sequence of operations of FIG. 9, in the sequence of operations of FIG. 10, when data from the pump is stored successfully by the MDS ("Yes" branch of decision block 360), the MDS prepares an acknowledgment for the pump (block 362) and determines whether packages are available, regardless of whether the pump has previously applied the available packages or not (block 364). When there are available packages ("Yes" branch of block 364), the MDS prepares a list of the available packages (block 366) and sends, to the pump, the acknowledgment and the list of available packages (block 368). In some embodiments, this list indicates a unique identifier for each of the available packages. When there are no available packages ("No" branch of block 364), the MDS simply sends the acknowledgment (block 370).

After the MDS quarantines data from the pump (block 356), after the MDS sends the acknowledgement as well as a list of available packages to the pump (block 368), or after the MDS sends the acknowledgment only (block 370), the sequence of operations of FIG. 10 ends.

The head of a syringe pump is configured to collect data associated with the operation of the pump at the following designated points in the head's work flow: at the selection of a drug program, at the end of an infusion, at a change of an infusion, at an alarm, at the clearing of an alarm, when the pump is powered on, before the pump is powered down, at a calibration of the pump, in response to an indication that maintenance is required, and at other user actions (such as interaction with the keypad of the head to override a data value). Some of this data represents status data (for example, status data may include an indication of the power source of the pump, the level of its energy storage device, the settings for an infusion) while other data represents event data (for example, event data may include alarm, fault, maintenance, therapy, therapy change, telemetry, and power events). Periodically, the base of the pump queries the head of the pump for data. If the head is not busy, it replies with the data. If the head is busy, the base waits and queries the head of the pump for data again. Upon receiving data from the head, the base stores that data in its log with an indication that the data has not been sent and prepares unsent data to be sent to the MDS.

Figure 11A:
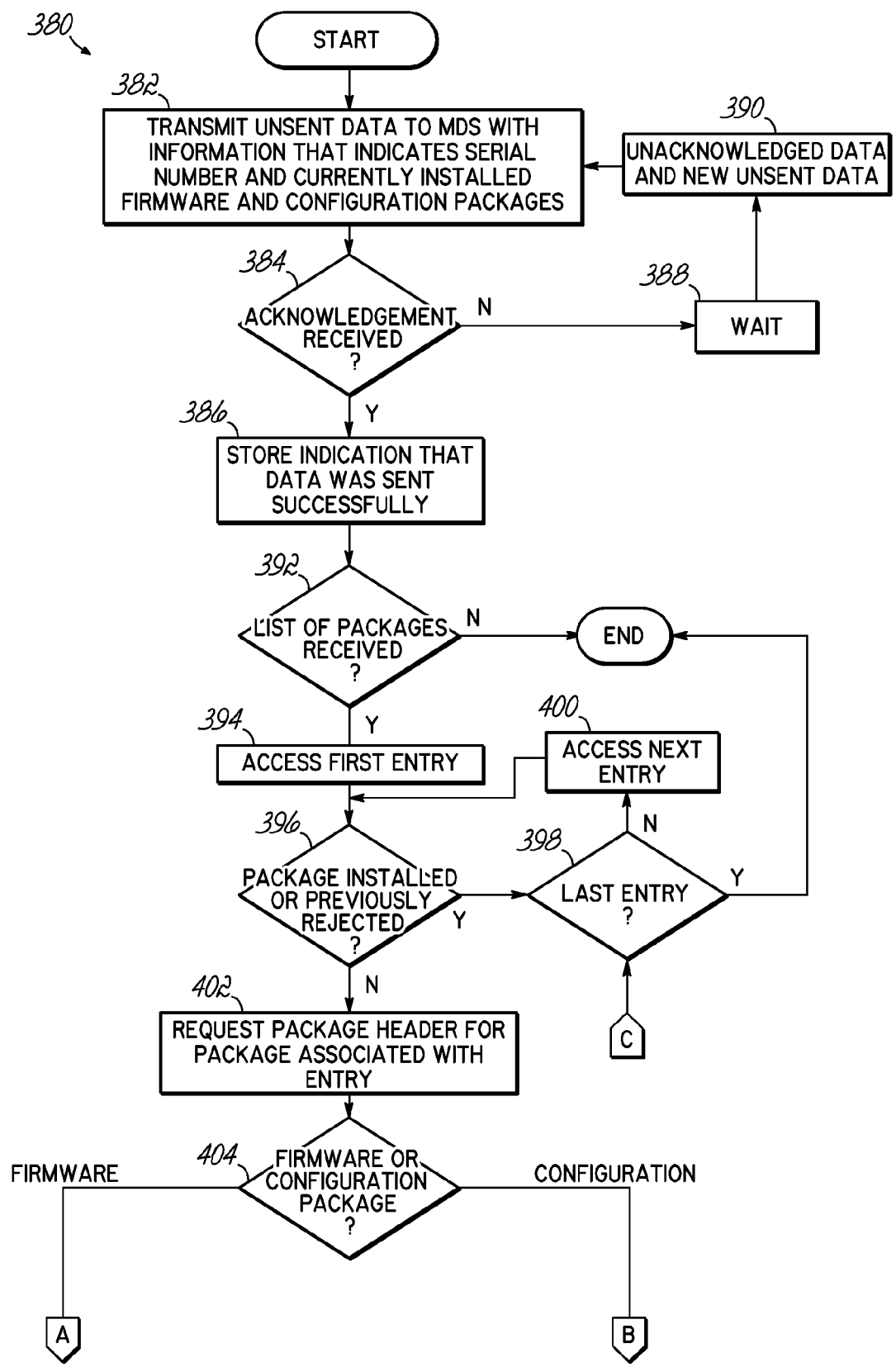
FIGS. 11A, 11B, and 11C are a flowchart illustrating a sequence of operations executable by the pump of FIG. 1 to determine the applicability of an available configuration and/or firmware package.
Figure 11B:
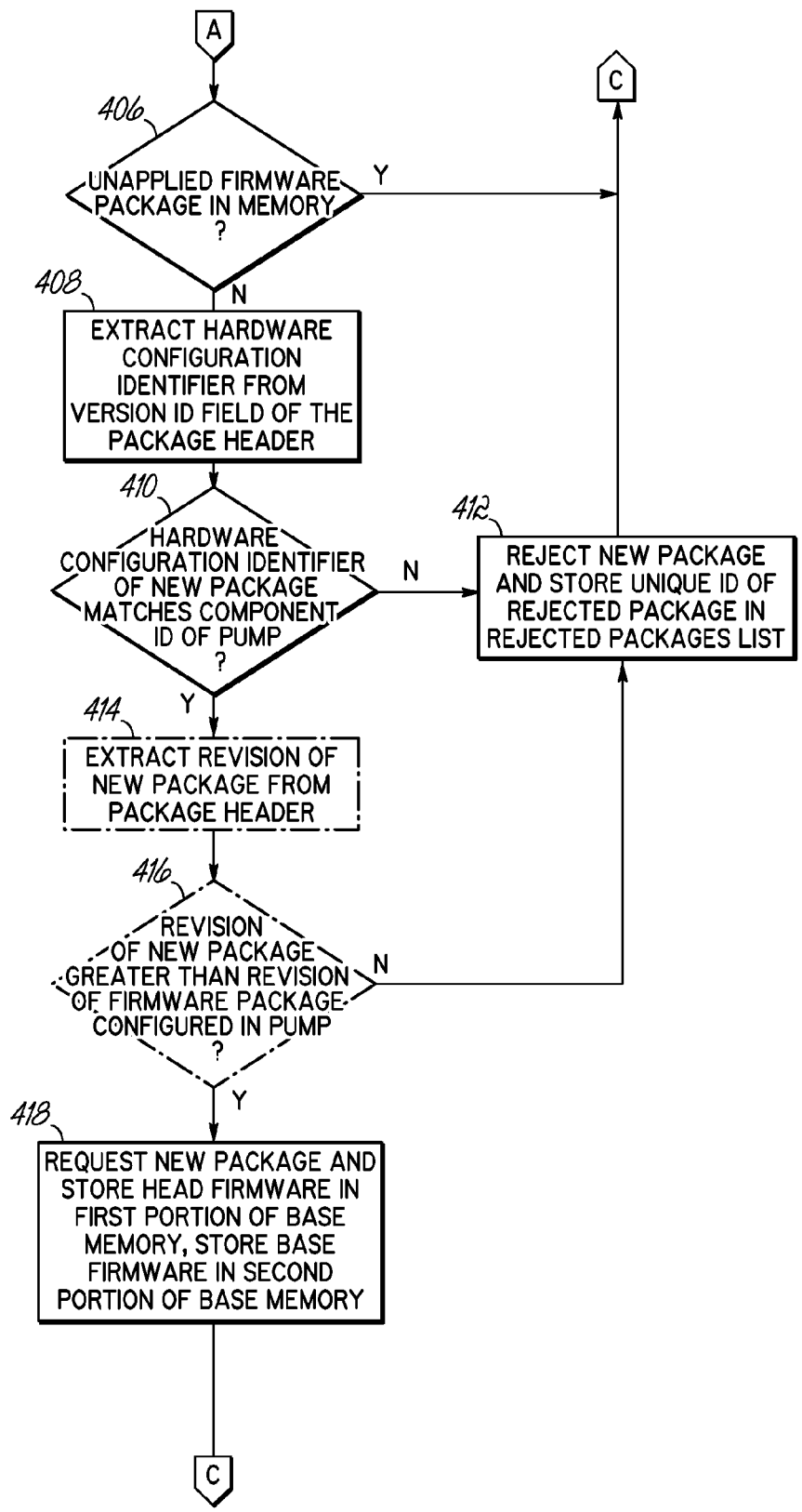
Figure 11C:
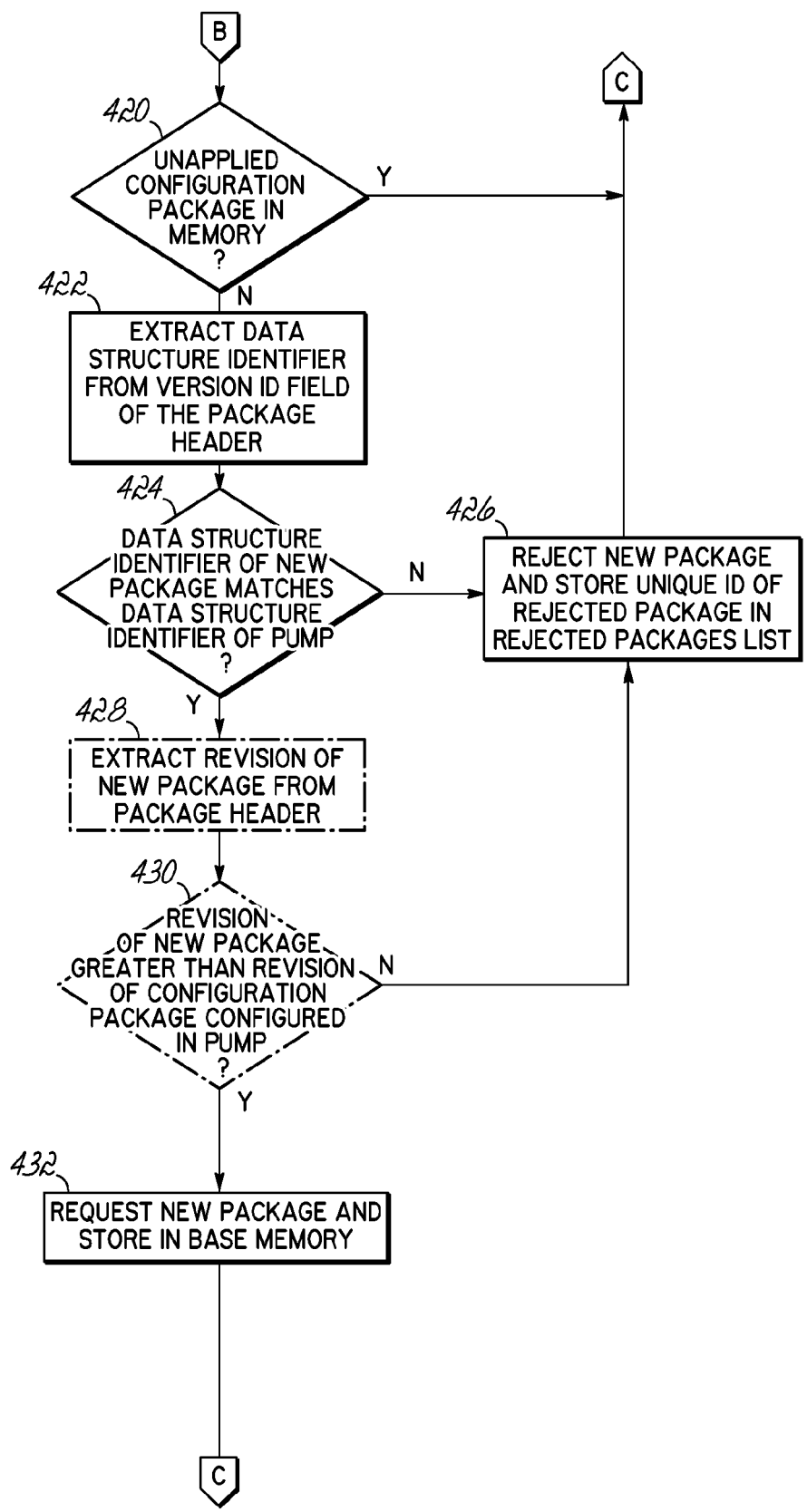

FIGS. 11A, 11B, and 11C are a flowchart 380 illustrating a sequence of operations for a pump, and in particular for a base of the pump and program code configured thereupon, to transmit data to the MDS and determine whether to download a new configuration or firmware package (e.g., a "new" configuration or firmware package is a configuration or firmware package that has not been previously installed, rejected, or stored in the base of the pump) consistent with embodiments of the invention. About every five seconds, the base gathers unsent data and transmits that data to the MDS with a header that indicates the serial number of the pump and currently installed firmware and configuration packages (block 382).

The base then determines if an acknowledgment of the data being stored successfully has been received (block 384). When the base receives an acknowledgment from the MDS that sent data has been stored successfully ("Yes" branch of decision block 384), the base indicates in its log that the data associated with that acknowledgment was sent successfully (block 386). Thus, data that is acknowledged will not be sent to the MDS again. When the base has not received an acknowledgment from the MDS ("No" branch of decision block 384), it waits for about one to two minutes (block 388) then re-sends the unacknowledged data to the MDS along with any new unsent data (block 390).

After storing an indication that data was sent successfully (block 386), the base determines whether a list of packages has been received (e.g., a list of available and unapplied packages sent from an MDS as per the sequence of operations of FIG. 9, or a list of available packages sent from an MDS as per the sequence of operations of FIG. 10) (block 392). When a list of packages has not been received ("No" branch of decision block 392) the sequence of operations of FIGS. 11A, 11B, and 11C ends. When a list of packages has been received ("Yes" branch of decision block 392), the base accesses the first entry of the list to determine a unique identifier for a package associated with the current entry (block 394) and compares that unique identifier to packages that are currently installed in the pump as well as a list of unique identifiers of previously rejected packages (block 396). For example, the base is configured to request additional information about packages that are not installed and packages that it has not previously rejected, while refraining from requesting additional information about packages that it has installed or previously rejected. As such, the base stores the unique identifiers of previously rejected packages in a list for future reference for that determination. Thus, when the base determines that a unique identifier of a package matches a unique identifier of an installed package or previously rejected package ("Yes" branch of decision block 396), the base determines whether that entry is the last entry of the list (block 398). When the entry is the last entry of the list of packages ("Yes" branch of decision block 398) the sequence of operations of FIGS. 11A, 11B, and 11C ends. When the entry is not the last entry of the list of packages ("No" branch of decision block 398) the base access the next entry of the list of packages (block 400) and again determines whether the unique identifier for the package associated with that entry matches a unique identifier of an installed package or a previously rejected package (block 396).

When the base determines that a unique identifier associated with a package does not match a unique identifier of an installed package or a previously rejected package ("No" branch of decision block 396), the package may be considered a "new" package that represents an update from the configuration or firmware package currently installed in the pump. Thus, the base requests a package header for the new package (block 402). In response to receiving the package header, the base determines, from a package type field of the package header, whether the new package is a firmware or configuration package (block 404). When the base determines that the new package is a firmware package ("Firmware" branch of decision block 404), the base determines if an unapplied firmware package is present in the base memory (block 406). When there is an unapplied firmware package present in the base memory ("Yes" branch of decision block 406), the base again determines whether the current entry on the list of packages from the MDS is the last entry (block 398) and proceeds as previously described. In this manner, if the pump has already downloaded an unapplied firmware package, it will not download another firmware package. When there is no unapplied firmware package present in the base memory ("No" branch of decision block 406) the base extracts a hardware configuration identifier of the new package from the version identification field of its package header (block 408) and determines whether the hardware configuration identifier associated with the new package matches the component identifier associated with the pump (block 410). When the hardware configuration identifier associated with the new package does not match the component identifier associated with the pump ("No" branch of decision block 410), the base rejects the firmware package and stores the unique identifier of the now rejected package in its rejected package list (block 412), then again determines whether the current entry on the list of packages from the MDS is the last entry (block 398) and proceeds as previously described.

In an optional block, when the hardware configuration identifier associated with the new package matches the component identifier associated with the pump ("Yes" branch of decision block 410), the base extracts revision identifier of the new package that indicates a particular revision of firmware with which that new package is associated from its package header (block 414). After extracting the revision identifier of the new package from its package header (block 414), and in another optional block, the base determines whether the revision identifier associated with the new package is greater than the revision identifier of a firmware package configured on the pump (block 416). When the revision identifier associated with the new package is not greater than the revision identifier of the firmware package configured on the pump ("No" branch of decision block 416), the base rejects the new package and stores the unique identifier of the now rejected package in its rejected package list (block 412) and proceeds as previously described.

Returning to block 410, when the hardware configuration identifier associated with the new package matches the component identifier associated with the pump ("Yes" branch of decision block 410) and/or, in the optional block, when the revision identifier associated with the new package is greater than the version identifier of the firmware package configured on the pump ("Yes" branch of decision block 416), the base requests the new package from the package server, stores the head firmware of the new package in a first portion of the base memory, and stores the base firmware of the new package in a second portion of the base memory such that the new package is stored as an unapplied firmware package in the base memory (block 418). In response to storing the new package in the base memory (block 418), the base again determines whether the current entry on the list of packages from the MDS is the last entry (block 398) and proceeds as previously described.

Returning to block 404, when the base determines that the new package is a configuration package ("Configuration" branch of decision block 404), the base determines if an unapplied configuration package is present in the base memory (block 420). When there is an unapplied configuration package present in the base memory ("Yes" branch of decision block 420), the base again determines whether the current entry on the list of packages from the MDS is the last entry (block 398) and proceeds as previously described. In this manner, if the pump has already downloaded an unapplied configuration package, it will not download another configuration package. When there is no unapplied configuration package present in the base memory ("No" branch of decision block 420) the base extracts a data structure identifier of the new package from the version identification field of its package header (block 422) and determines whether the data structure identifier associated with the new package matches the data structure identifier associated with the pump (block 424). When the data structure identifier associated with the new package does not match the data structure identifier associated with the pump ("No" branch of decision block 424), the base rejects the configuration package and stores the unique identifier of the now rejected package in its rejected package list (block 426), then again determines whether the current entry on the list of packages from the MDS is the last entry (block 398) and proceeds as previously described.

In an optional block, when the data structure identifier associated with the new package matches the data structure identifier associated with the pump ("Yes" branch of decision block 424), the base extracts a revision identifier of the new package that indicates a particular revision of configuration with which that new package is associated from its package header (block 428). After extracting the revision identifier of the new package from its package header (block 428), and in another optional block, the base determines whether the revision identifier associated with the new package is greater than the revision identifier of a configuration package configured on the pump (block 430). When the revision identifier associated with the new package is not greater than the revision identifier of the configuration package configured on the pump ("No" branch of decision block 430), the base rejects the new package and stores the unique identifier of the now rejected package in its rejected package list (block 426) and proceeds as previously described.

Returning to block 424, when the data structure identifier associated with the new package matches the data structure identifier associated with the pump ("Yes" branch of decision block 424) and/or, in the optional block, when the revision identifier associated with the new package is greater than the version identifier of the firmware package configured on the pump ("Yes" branch of decision block 430), the base requests the new package from the package server and stores the configuration package in its memory such that the new package is stored as an unapplied configuration package in the base memory (block 432). In response to storing the new package in the base memory (block 432), the base again determines whether the current entry on the list of packages from the MDS is the last entry (block 398) and proceeds as previously described.

Figure 12:
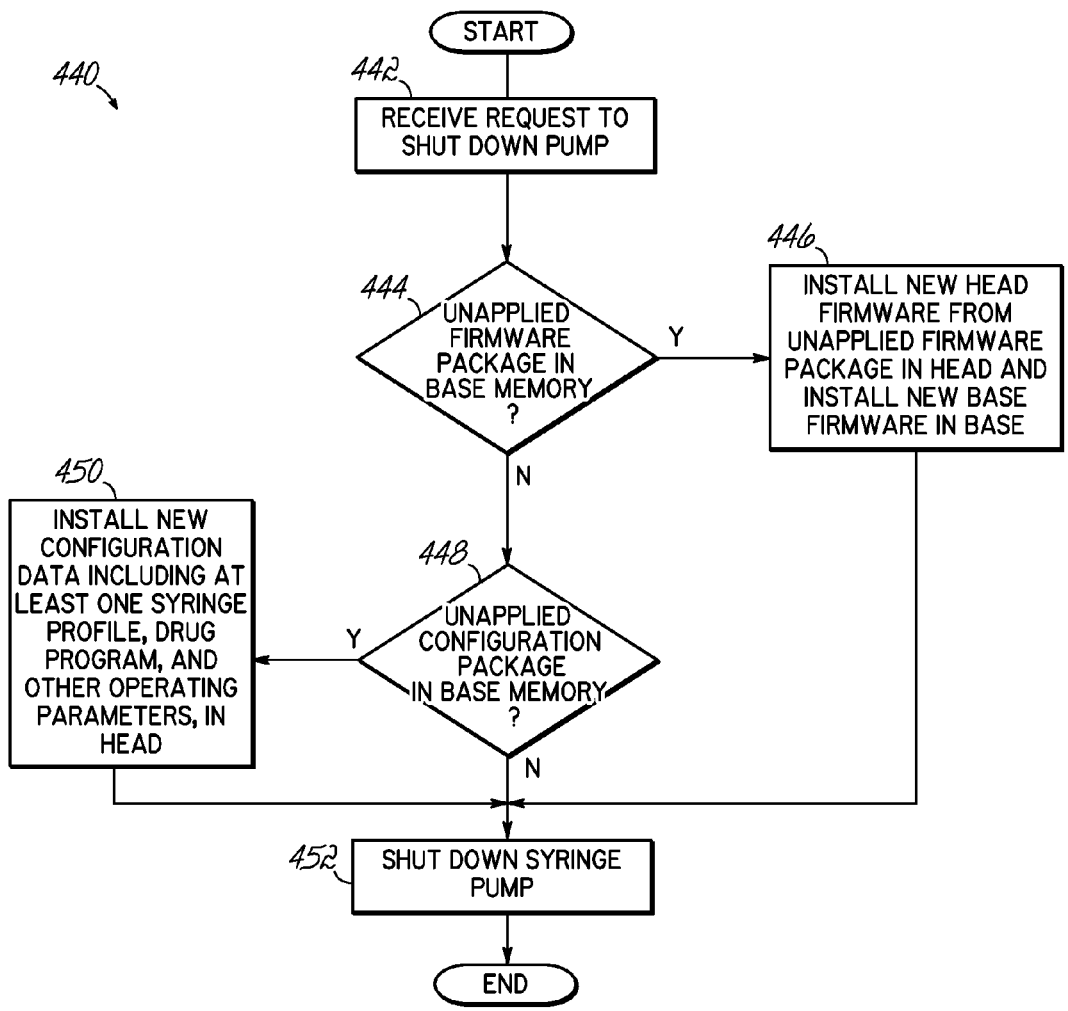
FIG. 12 is a flowchart illustrating a sequence of operations executable by the pump of FIG. 1 to install a configuration or firmware package.

FIG. 12 is a flowchart 440 illustrating a sequence of operations for a pump, and in particular for a base of the pump and program code configured thereupon, to install a configuration or firmware package consistent with embodiments of the invention. Specifically, the pump is configured to apply configuration or firmware package in response to a user shutting down the pump such that updates of the pump do not occur during an infusion. Thus, when the pump receives a request to shut down the pump (such as when a user presses a button on the head of the pump dedicated to initiate a shut-down sequence of the pump) (block 442) the base determines whether there is an unapplied firmware package in the base memory (block 444). When there is an unapplied firmware package in the base memory ("Yes" branch of decision block 444) the base installs the head firmware from the unapplied firmware package in the head and installs the base firmware from the unapplied firmware package in the base (block 446). When there is no unapplied firmware package in the base memory ("No" branch of decision block 444), the base determines whether there is an unapplied configuration package in the base memory (block 448).

When there is an unapplied configuration package in the base memory ("Yes" branch of decision block 448) the base installs the configuration package, including the at least one syringe profile, drug program, and other operating parameters of the configuration package, in the head (block 450). In response to installing a firmware package (block 446), determining that there is no unapplied configuration package in the base memory ("No" branch of decision block 448), or in response to installing a configuration package (block 452), the pump shuts down (block 452) and the sequence of operations of FIG. 12 ends.

While the present invention has been illustrated by a description of the various embodiments, and while these embodiments have been described in considerable detail, it is not the intention of the applicants to restrict or in any way limit the scope of the appended claims to such detail. Additional advantages and modifications will readily appear to those skilled in the art. Thus, the invention in its broader aspects is therefore not limited to the specific details, representative apparatus and method, and illustrative example shown and described. In particular, a person having ordinary skill in the art will appreciate that any of the blocks of the above flowcharts may be deleted, augmented, made to be simultaneous with another, combined, or be otherwise altered in accordance with the principles of the embodiments of the invention. Accordingly, departures may be made from such details without departing from the spirit or scope of applicants' general inventive concept.

Other modifications will be apparent to a person having ordinary skill in the art. Therefore, the invention lies in the claims hereinafter appended.

What is claimed is:

1. A method of updating a syringe pump for operation with a plurality of syringes to be used in a facility or portion thereof, the syringe pump adapted to support a syringe having a plunger therein, the syringe pump having a piston drive adapted to couple to the plunger, a processor operably coupled to control movement of the piston drive, and a memory adapted to store a plurality of syringe profiles for a plurality of different syringes, each syringe profile containing data for use by the processor to control movement of the piston drive in relation to a respective syringe in order to expel fluid therefrom at a rate, the method comprising:
   with a computing system containing a database of data correlated to an array of syringes for which the syringe pump could be used, culling from the database a plurality of syringe profiles for the syringes to be used by the syringe pump within the facility or portion thereof; and
   updating the memory of the syringe pump while in the facility with the culled plurality of syringe profiles whereby to update the syringe pump for operation with the syringes to be used with the syringe pump in the facility or portion thereof.

2. The method of claim 1, wherein the data of the database is an array of syringe profiles for the array of syringes, culling from the database comprising selecting the plurality of syringe profiles.

3. The method of claim 1, wherein the culled plurality of syringe profiles is fewer in number than the array of syringes.

4. The method of claim 1 further comprising obtaining a syringe file that defines the database and loading the database in a memory of the computing system.

5. The method of claim 4, wherein obtaining the syringe file includes obtaining the syringe file from a third party.

6. The method of claim 5, the method of obtaining the syringe file including obtaining a program product containing the syringe file, and loading the database including loading the database from the program product into the memory of the computing system.

7. The method of claim 1 further comprising obtaining the computing system with the database loaded therein.

8. The method of claim 1, wherein culling the plurality of syringe profiles from the database includes displaying a list of the array of syringes and selecting from the displayed array a plurality of syringes to be used by the syringe pump in the facility or portion thereof such that respective syringe profiles associated with the selected plurality of syringes are automatically culled from the database.

9. A system for updating a syringe pump, comprising:
a syringe pump for operation with a plurality of syringes to be used in a facility or portion thereof, the syringe pump adapted to support a syringe having a plunger therein, the syringe pump having a piston drive adapted to couple to the plunger, a processor operably coupled to control movement of the piston drive, and a memory adapted to store a plurality of syringe profiles for a plurality of different syringes, each syringe profile containing data for use by the processor to control the movement of the piston drive in relation to a respective syringe in order to expel fluid therefrom at a rate; and
a computing system containing a database of data correlated to an array of syringes for which the syringe pump could be used, the computing system configured to cull from the database a plurality of syringe profiles for the syringes to be used by the syringe pump within the facility or portion thereof,
wherein the memory of the syringe pump is updated while in the facility with the culled plurality of syringe profiles whereby to update the syringe pump for operation with the syringes to be used with the syringe pump in the facility or portion thereof.

10. The system of claim 9, wherein the data of the database is an array of syringe profiles for the array of syringes, and wherein the computing system is further configured to select the plurality of syringe profiles from the array of syringe profiles.

11. The system of claim 9, wherein the culled plurality of syringe profiles is fewer in number than the array of syringes.

12. The system of claim 9, wherein the computing system is further configured to obtain a syringe file that defines the database and load that database in a memory of the computing system.

13. The system of claim 12, wherein the computing system is further configured to obtain the syringe file from a third party.

14. The system of claim 13, wherein the computing system is further configured to obtain the syringe file from a program product containing the syringe file, and wherein the computing system is configured to load the database from the program product into the computing system memory.

15. The system of claim 9, wherein the computing system is obtained with the database loaded therein.

16. The system of claim 9, wherein the computing system is further configured to cull the plurality of syringe profiles from the database by displaying a list of the array of syringes and selecting from the displayed array a plurality of syringes to be used by the pump in the facility or portion thereof such that respective syringe profiles associated with the selected plurality of syringes are automatically culled from the database.

17. A method of updating a syringe pump for operation with a plurality of syringes to be used in a facility or portion thereof, the syringe pump including a housing adapted to support a syringe having a plunger therein, a piston drive adapted to couple to the plunger, a processor operably coupled to control movement of the piston drive, and a memory adapted to store a plurality of syringe profiles for a plurality of different syringes to be used by the syringe pump within a facility or portion thereof, each syringe profile containing data for use by the processor to control movement of the piston drive in relation to a respective syringe in order to expel fluid therefrom at a rate, the method comprising:
receiving a plurality of syringe profiles for the syringes to be used by the syringe pump within the facility or portion thereof, the plurality of syringe profiles culled from a database of data correlated to an array of syringes for which the syringe pump could be used;
updating the memory of the syringe pump with the culled plurality of syringe profiles whereby to update the syringe pump for operation with the syringes to be used with the syringe pump in the facility or portion thereof.

18. The method of claim 17, wherein the data of the database is an array of syringe profiles for the array of syringes, the culled plurality of syringe profiles selected from the array of syringe profiles.

19. The method of claim 17, wherein the culled plurality of syringe profiles is fewer in number than the array of syringes.

20. The method of claim 17, wherein the culled plurality of syringe profiles are configured in a configuration package for updating the memory of the syringe pump.

21. The method of claim 17, wherein the syringe pump includes a keypad and a display, and wherein updating the memory of the syringe pump includes:
in response to a user request to shut down the syringe pump determined from user interaction with the keypad, displaying a query regarding installation of the culled plurality of syringe profiles; and
in response to receiving an indication to proceed with the installation of the culled plurality of syringe profiles determined from user interaction with the keypad, updating the memory of the syringe pump.

22. A syringe pump, comprising:
a housing adapted to support a syringe having a plunger therein;
a piston drive adapted to couple to the plunger;
a processor operably coupled to control movement of the piston drive;
a memory adapted to store a plurality of syringe profiles for a plurality of different syringes to be used by the syringe pump within a facility or portion thereof, each syringe profile containing data for use by the processor to control movement of the piston drive in relation to a respective syringe in order to expel fluid therefrom at a rate, the memory further including program code to update the syringe pump, the program code configured to, while the syringe pump is in the facility or portion thereof, receive the plurality of syringe profiles for the syringes to be used by the syringe pump within the facility or portion thereof, the plurality of syringe profiles culled from a database of data correlated to an array of syringes for which the syringe pump could be used, the program code further configured to update the memory of the syringe pump with the culled plurality of syringe profiles whereby to update the syringe pump for operation with the syringes to be used with the syringe pump in the facility or portion thereof.

23. The syringe pump of claim 22, wherein the data of the database is an array of syringe profiles for the array of syringes, the culled plurality of syringe profiles selected from the array of syringe profiles.

24. The syringe pump of claim 22, wherein the culled plurality of syringe profiles is fewer in number than the array of syringes.

25. The syringe pump of claim 22, wherein the culled plurality of syringe profiles are configured in a configuration package for updating the memory of the syringe pump.

26. The syringe pump of claim 22 further comprising a keypad and a display, wherein the program code is further configured to display a query regarding installation of the culled plurality of syringe profiles in response to a request to shut down the syringe pump determined from user interaction with the keypad and, the program code further configured to update the memory of the syringe pump in response to receiving an indication to proceed with the installation of the culled plurality of syringe profiles determined from user interaction with the keypad.

* * * * *